(12) United States Patent
Degenhardt et al.

(10) Patent No.: US 6,208,460 B1
(45) Date of Patent: Mar. 27, 2001

(54) OPTICAL HEAD

(75) Inventors: Keith Raymond Degenhardt, Willunga; Victor Konrad Previn, Ashton, both of (AU)

(73) Assignee: Taracan Pty Ltd., Adelaide (AU)

( * ) Notice: Subject to any disclaimer, the term of this patent is extended or adjusted under 35 U.S.C. 154(b) by 0 days.

(21) Appl. No.: 09/366,863

(22) Filed: Aug. 4, 1999

(30) Foreign Application Priority Data

Aug. 7, 1998 (AU) ................................................... PP 5107

(51) Int. Cl.$^7$ ................................................... G02B 21/06
(52) U.S. Cl. .................... 359/385; 359/386; 359/387; 359/388; 359/389
(58) Field of Search ..................... 359/385, 386, 387, 388, 389, 390; 351/205, 208, 209, 210–216, 243, 7, 14

(56) References Cited

U.S. PATENT DOCUMENTS

| | | | |
|---|---|---|---|
| 3,944,342 | * | 3/1976 | Martinez ................................ 351/14 |
| 4,644,550 | * | 2/1987 | Csery et al. .......................... 372/40 |
| 4,744,649 | * | 5/1988 | Niino et al. .......................... 351/221 |
| 4,862,886 | * | 9/1989 | Clarke et al. ....................... 128/303.1 |
| 5,488,443 | * | 1/1996 | Ota et al. ............................... 351/221 |
| 5,513,239 | * | 4/1996 | Mulder ................................ 378/98.7 |

OTHER PUBLICATIONS

Gish Biomedical, Inc. brochure for YAG laser systems.
The Sharplan 702 Nd:YAG Laser brochure.

* cited by examiner

*Primary Examiner*—Mohammad Y. Sikder
(74) *Attorney, Agent, or Firm*—Merchant & Gould P.C.

(57) ABSTRACT

A removable head for an ophthalmic slit lamp assembly that replaces the conventional slit lamp microscope with a laser and binocular microscope combination. The optic axis of the laser is aligned to the optic axis of the binocular microscope so the optical head can be removed and used with another slit lamp assembly.

An adaptor provides adjustable connection between the optical head and a microscope support arm of the slit lamp assembly. The adaptor consists of a base member and a frame member. The frame member is rotated and translated relative to the base member to align the optic axis of the optical head to the slit lamp optic axis.

11 Claims, 8 Drawing Sheets

OPTICAL HEAD

This invention relates to an improved optical head for an ophthalmic slit lamp microscope. In particular, it relates to an optical head that incorporates a treatment laser and a binocular eyepiece.

BACKGROUND TO THE INVENTION

Ophthalmic microscopes are essential instruments that can be found in the rooms of every ophthalmologist and optometrist. The most common models are those made by Haag Streit and Zeiss. Although other manufacturers exist, such as CSO, their microscopes generally follow the design of one of these two producers.

All ophthalmic microscopes have a number of common elements in their design. They all consist of a base with a support frame for positioning the eye of a patient. The frame has a chin rest and a forehead strap that together position the patient's head in a central position that allows easy viewing of the eye. A slit lamp and binocular microscope are mounted on a swivel base that allows adjustment of the apparatus to focus on either the left or right eye.

Depending on the manufacturer and model, the slit lamp may be mounted above, below or beside the binocular head. The slit lamp is adjustable to focus a slit of light on the retina of a patient. The focus of the binocular microscope may also be adjusted to focus on the part of the eye requiring attention.

Whatever the optic configuration, it is essential that the optical components are correctly aligned. The optical accuracy required makes these instruments expensive and delicate.

Lasers have found application in treatment of the eye. In the early days of laser eye treatments the lasers were relatively large and cumbersome. However, recent advances in technology have resulted in very compact lasers with relatively high power. It is now possible to produce a laser with sufficient power for many eye treatments that is small enough to mount on a slit lamp microscope. A number of different mounting arrangements have been proposed.

In one scheme, the laser is mounted beneath the base of the microscope with the beam directed upwards. The beam is steered by prisms to a partial mirror in front of the slit lamp microscope and light tower. This arrangement requires separate alignment and focusing of the laser beam to the optic axis of the slit lamp. A variation of this design has the prisms integrated to the light tower so that the laser beam moves with the slit lamp beam.

In a few prior art arrangements, small, lightweight lasers have been mounted directly on the slit lamp light tower. These designs are functionally similar to the above design but with the advantage of less optical elements being required. However, the arrangement compromises the independence of the illumination angle of the light source which can result in reduced visibility. For example, to optimally illuminate an ocular structure it is frequently necessary to illuminate non-coaxially. As the angle increases, the aperture of the illumination source is increased by the human iris. Aperturing of the slit lamp image is quite acceptable but aperture of the laser beam results in beam clipping which is undesirable. It is preferable to lock the laser axis to the viewing axis and leave the illumination axis unconstrained.

In another design, the laser is mounted above, below or beside the binocular microscope with the beam directed to a partial mirror before the objective lens of the microscope. This arrangement has the advantage of aligning the optic axis of the laser with the view of the ophthalmologist. However, if the alignment is truly coaxial, the slit lamp head will block the laser beam. This design therefore has the problem of the optic axis of the slit lamp and the laser beam being slightly displaced.

It will be appreciated that each of the generic designs described above require permanent attachment of the laser to the slit lamp in order to achieve and maintain correct optic alignment. This requires a substantial financial investment for the ophthalmologist since each slit lamp must have a dedicated laser. It is typical for an ophthalmologist to visit a number of surgeries, so multiple laser units may be required. The required investment is beyond the reach of many practitioners so that laser ophthalmology is not as common as it could be.

OBJECT OF THE INVENTION

It is an object of the present invention to provide an optical head which can be removably mounted to an ophthalmic slit lamp microscope. Further objects will be evident from the following discussion.

DISCLOSURE OF THE INVENTION

In one form, although it need not be the only or indeed the broadest form, the invention resides in a removable optical head for an ophthalmic slit lamp assembly, the optical head comprising:

a laser head emitting laser radiation along a laser optic axis;

a coupled to the laser head; and a power supply providing power to the laser head;

wherein the laser optic axis and a binocular optic axis of said binocular microscope head are aligned.

The optical head may further include control means for controlling operation of the laser head including power, exposure time, pulse duration and other parameters.

In a further form, the invention resides in a removable optical head for an ophthalmic slit lamp assembly, the optical head comprising:

a laser head emitting laser radiation along a laser optic axis;

a binocular microscope head coupled to the laser head; and an adaptor removably coupling the optical head to the ophthalmic slit lamp assembly;

wherein the laser optic axis and a binocular optic axis of said binocular microscope head are aligned; and wherein the adaptor includes adjustment means permitting adjustment of the optical head relative to the ophthalmic slit lamp assembly to align the laser optic axis and the binocular optic axis to an optic axis of a slit lamp of the slit lamp assembly.

In preference, the optical head further incorporates a power supply providing power to the laser head and may include control means for controlling operation of the laser head including power, exposure time, pulse duration and other parameters.

In preference, the adaptor is formed from a base member and a frame member, said frame member being movable relative to said base member. The relative movement between the base member and the frame member is suitably translational movement.

Rotational movement is suitably provided between the optical head and the ophthalmic slit lamp assembly. The rotational movement is suitably provided between the base member and the frame member.

In preference, an underside of the base member is shaped to match a shape of a top portion of a microscope support arm of the slit lamp assembly.

In combination, a removable optical head, an ophthalmic slit lamp assembly, and an adaptor removably coupling the optical head to the ophthalmic slit lamp assembly, said optical head comprising a laser head emitting laser radiation along a laser optic axis, a binocular microscope head coupled to the laser head, and a power supply providing power to the laser head, wherein the laser optic axis and a binocular optic axis are aligned, and wherein the adaptor includes adjustment means permitting adjustment of the optical head relative to the ophthalmic slit lamp assembly to align the laser optic axis and the binocular optic axis to an optic axis of a slit lamp of the slit lamp assembly A method of aligning a removable optical head to a slit lamp assembly, said optical head comprising a laser head emitting laser radiation along a laser optic axis and a binocular microscope head coupled to the laser head and wherein the laser optic axis and a binocular optic axis are aligned, the method including the steps of:

removing a microscope from a microscope support arm of the slit lamp assembly;

coupling an adaptor to the optical head, said adaptor comprising a base member and a frame member, said frame member being rotatable and translatable relative to said base member;

coupling the adaptor and optical head to the microscope support arm;

rotating and translating the optical head relative to the microscope support arm until the laser optic axis is aligned to an optic axis of a slit lamp of the slit lamp assembly.

BRIEF DETAILS OF THE DRAWINGS

DETAILED DESCRIPTION OF THE INVENTION

Figure 1:
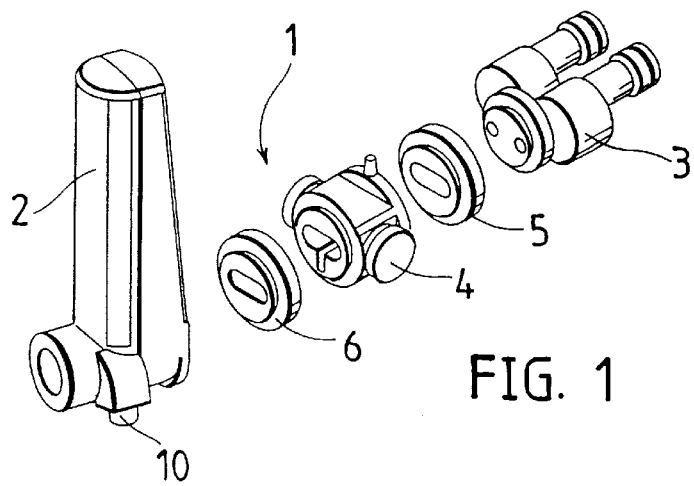
FIG. 1 shows an exploded view of the optic head.

Referring to FIG. 1 there is shown an exploded view of an optical head, generally indicated as 1. The optical head 1 includes a compact Nd:YAG laser 2 emitting a near infrared beam suitable for optic surgery. A binocular 3 is mounted to a magnification changer 4 with interface plate 5 which is in turn mounted to the laser with interface plate 6.

Figure 2:
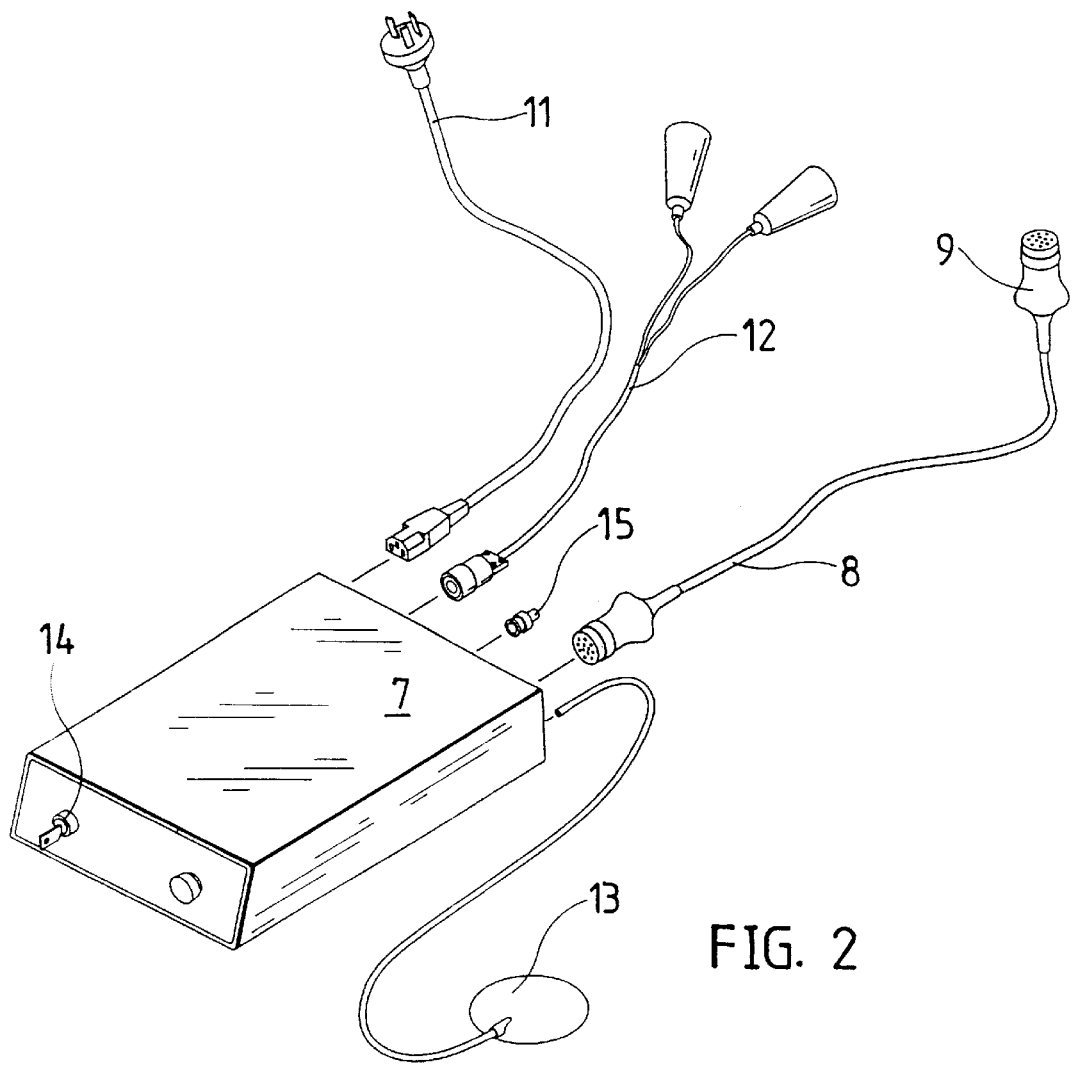
FIG. 2 is a sketch of a power supply for the optic head.

A power supply 7 (shown in FIG. 2) provides power to the laser head 1 through cable 8. The end 9 of the cable 8 plugs to the laser head 1 at socket 10. A 240 V power cord 11 is provided as well as a battery cord 12 for optional 12 V battery operation. The power supply 7 may be operated by foot switch 13 after a key switch 14 is activated. A safety interlock is also provided at the rear of the power supply although this may be deactivated with interlock shorting plug 15.

Figure 3:
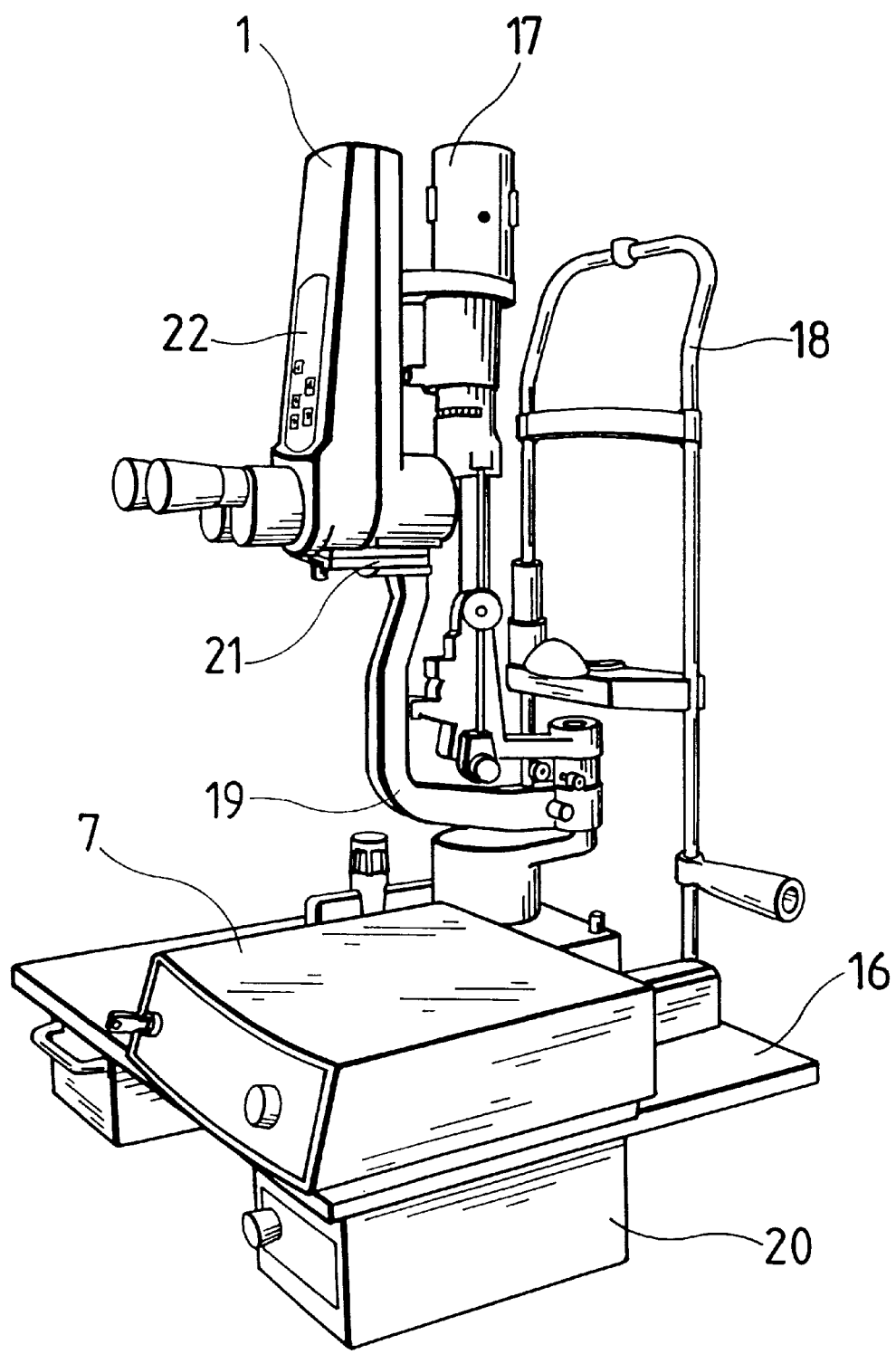
FIG. 3 shows a prior art CSO slit lamp assembly with the invention fitted.

The optical head 1 is shown fitted to a CSO 990 slit lamp assembly in FIG. 3. The slit lamp assembly consists of a table 16 upon which is mounted a frame including a slit lamp 17, chin rest 18 and microscope support arm 19. The slit lamp power supply 20 is mounted under the table.

The optical head 1 is mounted on the microscope support arm 19 in place of the microscope normally supplied with the slit lamp assembly. An adaptor 21 is provided between the support arm 19 and the optical head 1. The optical head does not interfere with the slit lamp 17 or the chin rest frame 18. The optical head power supply 7 is conveniently mounted on top of the table 16. As can be seen in FIG. 3, control panel 22 is provided on the optical head for control of the operation of the laser.

Figure 4:
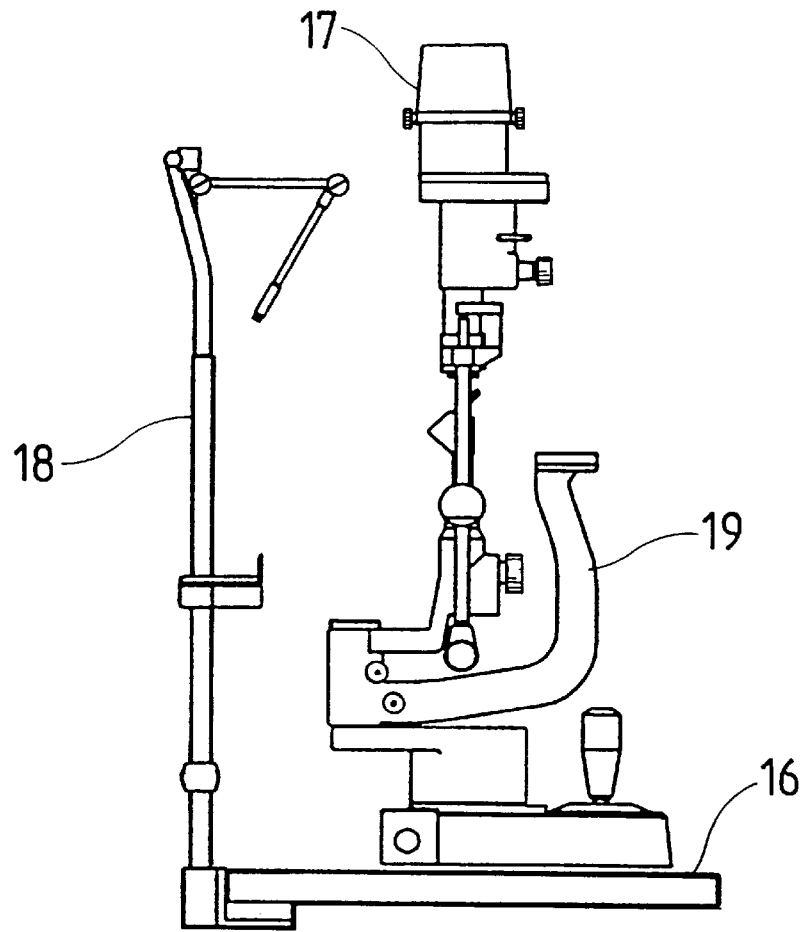
FIG. 4 shows a schematic side view of the slit lamp assembly of FIG. 3.
Figure 5:
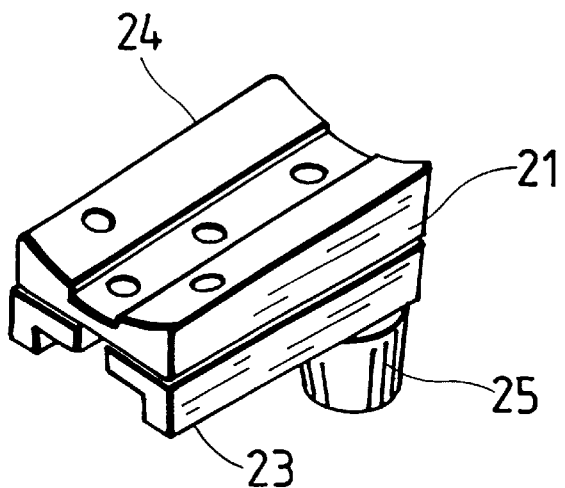
FIG. 5 shows a perspective view of the adaptor from FIG. 3.

A schematic side view of the CSO 990 slit lamp assembly is shown in FIG. 4. The adaptor 21 mounts the optical head 1 to the support arm 19 in the manner shown in FIG. 3. The adaptor 21 is shown in greater detail in FIG. 5.

The adaptor 21 consists of a base member 23, a frame member 24 and a locking screw 25. The underside of the base member 23 is shaped to fit the top of the support arm 19 and the top side of the frame member 24 is shaped to fit the underside of the optical head 1. The frame member 24 is moveable with respect to the base member 23 for alignment of the optical head to the slit lamp assembly. The frame member 24 is slid backwards or forwards with respect to the base member 23 in order to achieve the correct focus. The frame member 24 is able to rotate with respect to the base member 23 in order to rotate the optical head 1 until the optic axis of the optical head aligns with the optical axis of the slit lamp. The combination of sliding and rotation gives two degrees of freedom which allows quick and accurate alignment of the optical head 1 to the optic axis of the slit lamp 17. When correctly aligned the locking screw 25 is tightened to prevent relative movement between the base member 23 and the frame member 24.

Figure 6:
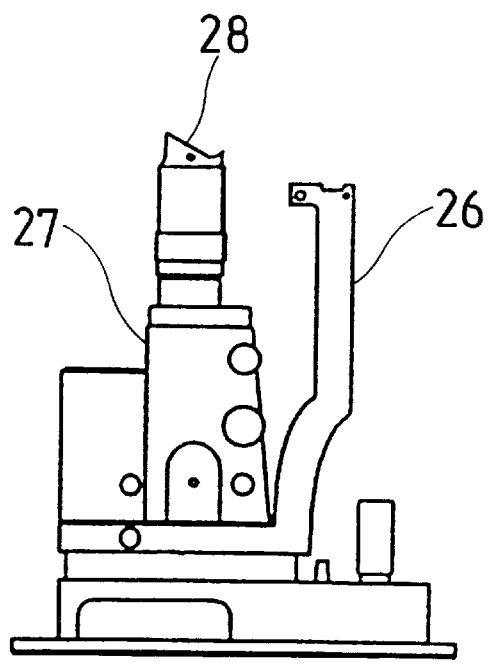
FIG. 6 shows a side view of a prior art Zeiss slit lamp assembly.

As mentioned previously, slit lamp assemblies come in a variety of configurations depending on the preferred design of the manufacturer. A side view of a Zeiss 30SL slit lamp assembly is shown in FIG. 6A. A microscope support arm 26 normally supports a microscope (removed in FIG. 6). The slit lamp 27 projects a light beam upwards for reflection from a mirror 28.

Figure 7:
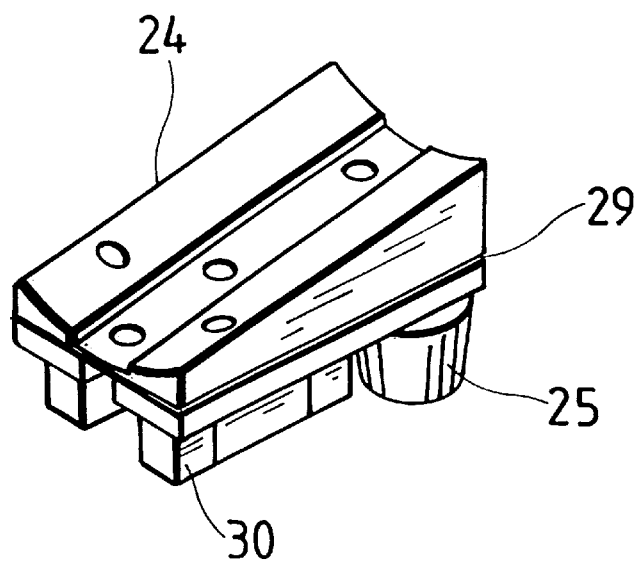
FIG. 7 shows a perspective view of an adaptor for the Zeiss slit lamp assembly of FIG. 6.

A suitable adaptor 29 for the Zeiss slit lamp assembly is shown in FIG. 7. As with the embodiment of FIG. 5, the adaptor 29 consists of a base member 30 and frame member 24. The shape of the base member 30 is suitable for attachment to the Zeiss slit lamp assembly of FIG. 6 and therefore has a different shape to the base member 23 shown in FIG. 5. Nonetheless, the adaptor 29 allows alignment of the optical head 1 to the slit lamp 27 in the same manner as the adaptor 21 described above.

Figure 8:
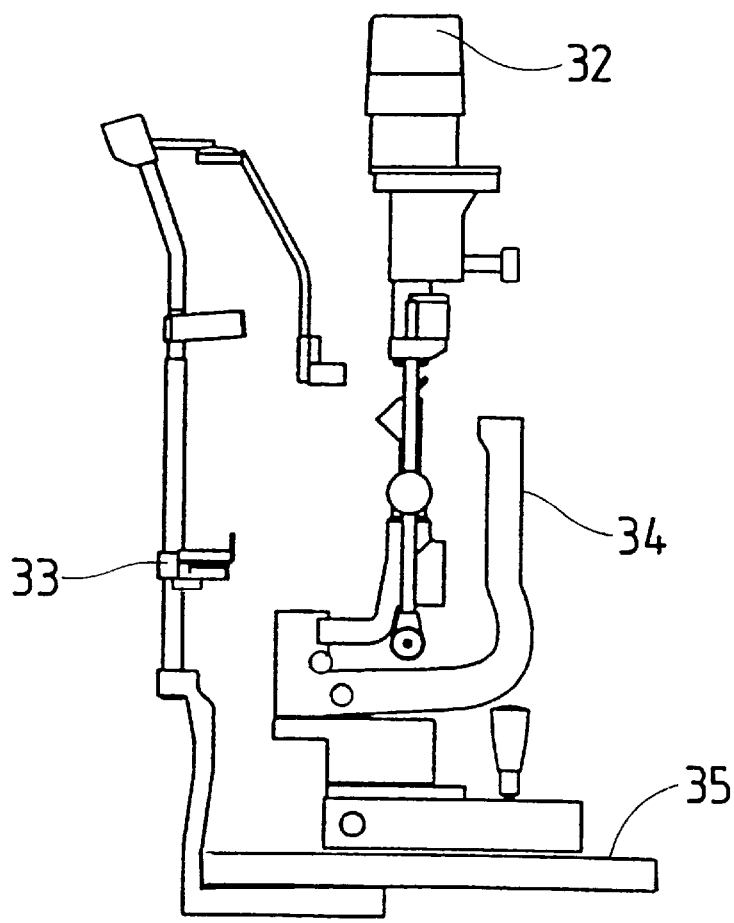
FIG. 8 shows a side view of a prior art Haag Streit slit lamp assembly.

The method of fitting and aligning the optical head to the slit lamp assembly will now be described with reference to a Haag Streit 900 slit lamp assembly, shown in FIG. 8 (with microscope removed). The slit lamp assembly has similar construction to the CSO slit lamp assembly described above. The slit lamp assembly consists of a slit lamp 32, chin rest 33, microscope support arm 34 and table 35.

Figure 9:
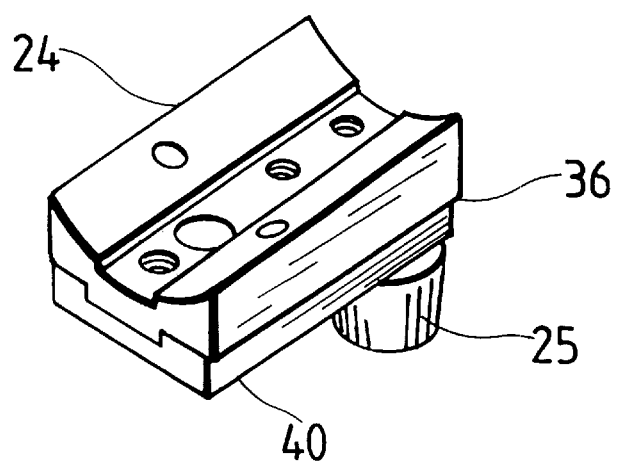
FIG. 9 shows a perspective view of an adaptor for the Haag Streit slit lamp assembly of FIG. 8.
Figure 10:
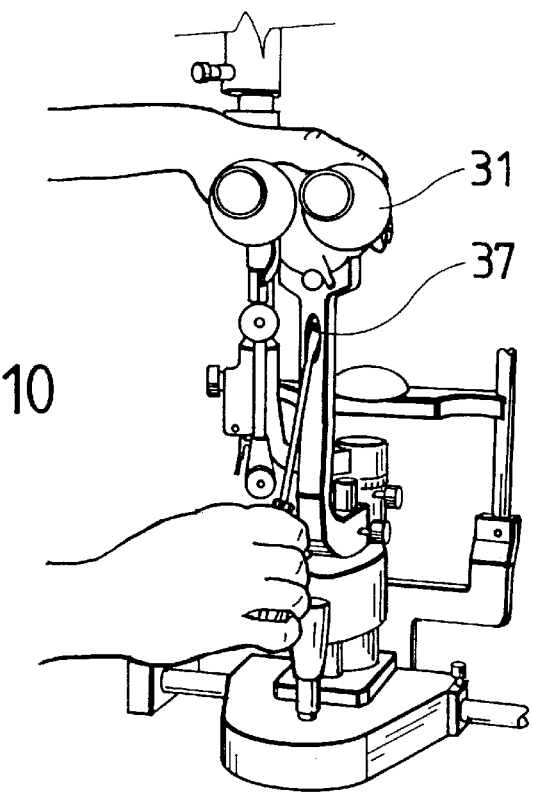
FIG. 10 shows removal of the microscope head from the slit lamp assembly.
Figure 11:
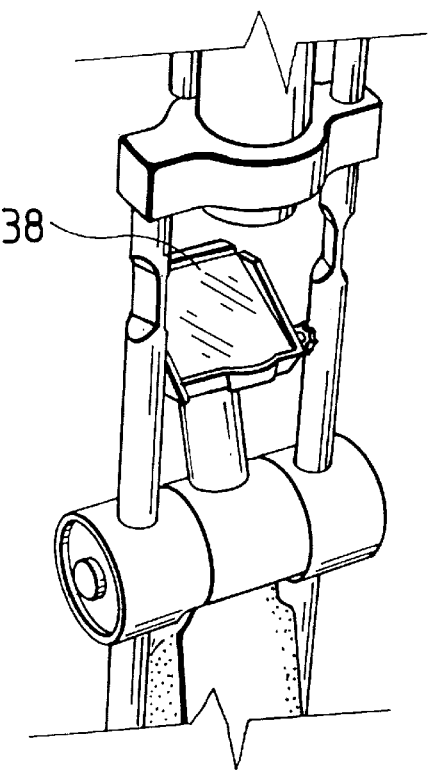
FIG. 11 shows the rectangular mirror in place.
Figure 12:
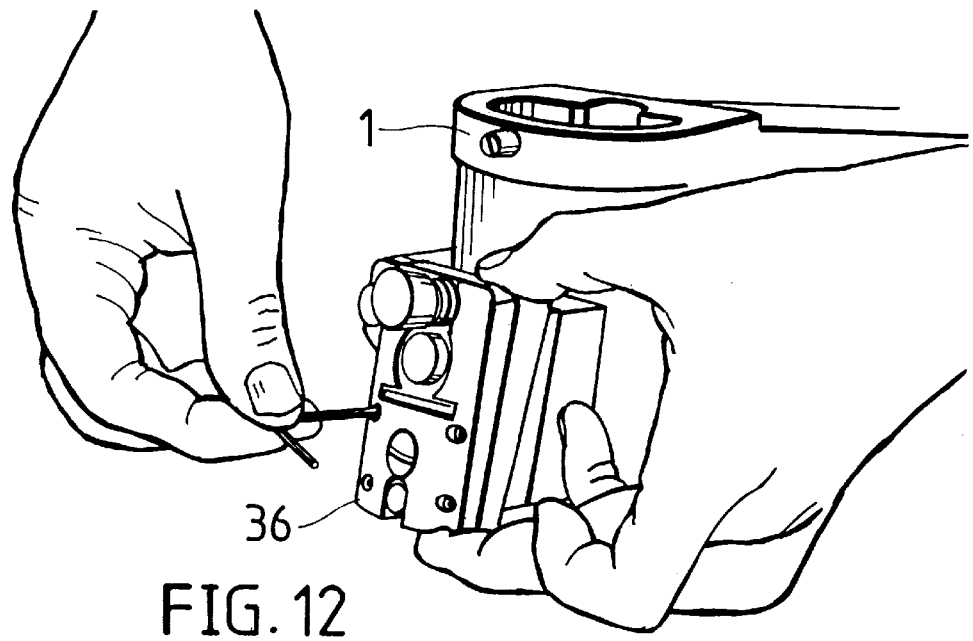
FIG. 12 shows the adaptor being fitted to the optical head.

The first step is to remove the existing microscope head 31 by unscrewing the angled attachment screw 37, as shown in FIG. 10. The slit lamp mirror is removed and replaced by a rectangular mirror 38 (see FIG. 11) that avoids beam clipping. The Haag Streit adaptor 36, shown in FIG. 9, is attached to the optical head 1 in the manner depicted in FIG. 12 with the frame member 24 in contact with the bottom of the optical head. The power supply 7 is then placed on or attached to the table 35.

The power supply connections are made including connecting the optical head 1 to the power supply 1, connecting the power supply to mains or battery power, isolating the interlock and connecting the foot switch 13. A focus post is mounted on the slit lamp assembly in a socket at the base of the illumination tower, in conventional manner. The slit lamp is turned on and adjusted to project a narrow, vertical image onto to focus post. At this stage the slit lamp assembly is prepared for receiving the optical head.

Figure 13:
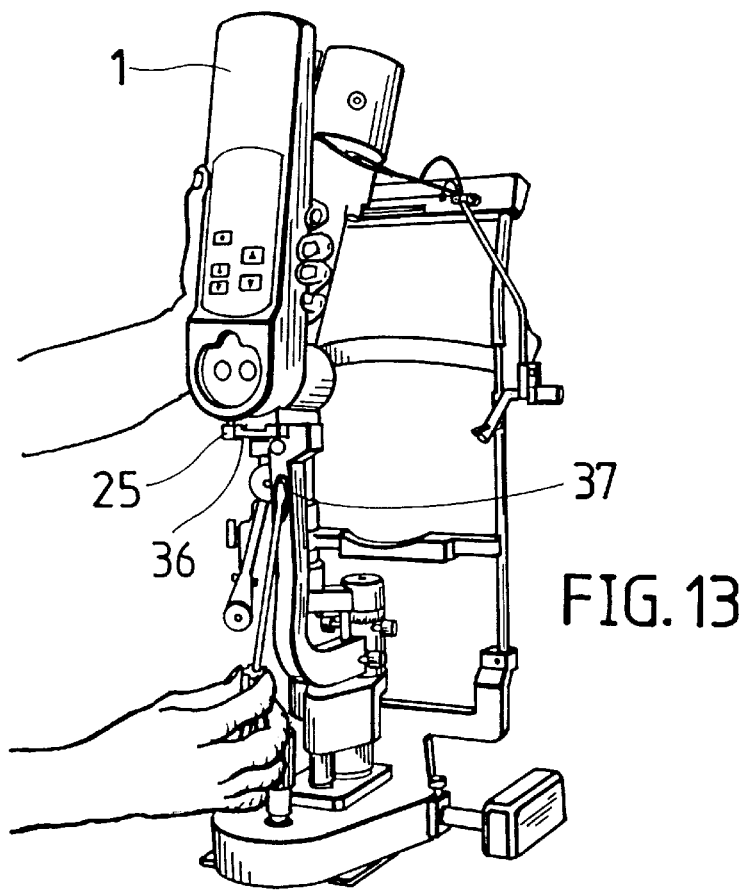
FIG. 13 shows the optical head and adaptor being fitted to a slit lamp assembly.

The optical head 1 is fitted to the support arm 34 by sliding the shaped underside of the base member 40 onto the corresponding portion of the support arm 34 and screwing in the angled attachment screw 37, as shown in FIG. 13. The binocular 3 may be removed from the optical head 1 during fitting, as shown. A normal seating position is adopted and the interpupillary distance of the binoculars is adjusted. The binocular eyepieces are adjusted to account for refractory variations of the operators eyes.

Figure 14:
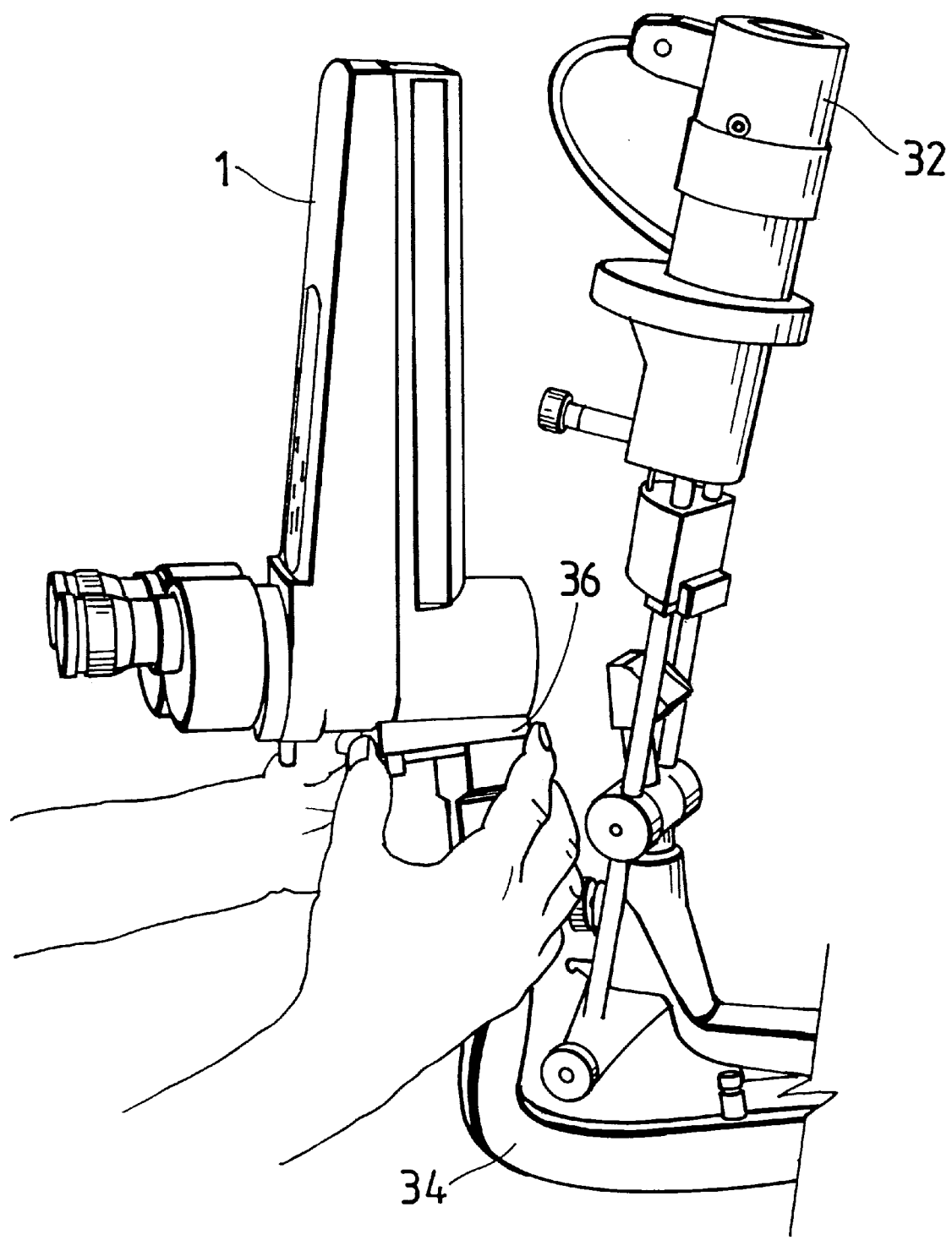
FIG. 14 shows the method of alignment.

To aid with alignment the optical head 1 may be provided with two alignment beams. Correct focus is achieved when the two aiming beams converge to one small spot centered on the slit lamp image. Focus is achieved by loosening the locking screw 25 and sliding the frame member 24 backwards and forwards with respect to the base member 40 until correct alignment is obtained. To position the spot on the slit lamp image the optical head 1 is rotated left or right. Once correct alignment is achieved the locking screw 25 is tightened to lock the optical head in position. The method of adjustment is shown in FIG. 14.

It will be appreciated that the primary value of the invention is in the easy fitting of the optical head to existing ophthalmic slit lamp microscopes. An ophthalmologist is able to purchase a single optical head which may then be transported to each slit lamp location. Upon arrival the optical head is fitted to the slit lamp in the normal position of the binocular microscope. Sliding and rotation adjustment is made to align the optical head to the slit lamp axis and the system is ready for operation. This is achieved by combining the binocular microscope and laser into a single element with a single optic axis that is quick and easy to align to the optic axis of the slit lamp assembly.

The optical head can be fitted to any existing slit lamp microscope with an appropriate adaptor. In a practice with a variety of equipment it is only necessary to purchase multiple adaptors rather than multiple optical heads or multiple ophthalmic slit lamp microscopes. In each case the existing microscope is removed, the adaptor is fitted, the optical head is fitted and alignment is made.

Throughout the specification the aim has been to describe the preferred embodiments of the invention without limiting the invention to any one embodiment or specific collection of features.

What we claim is:

1. A removable optical head for an ophthalmic slit lamp assembly, the optical head comprising:

a laser head emitting laser radiation along a laser optic axis;

a binocular microscope head coupled to the laser head; and an adaptor removably coupling the optical head to the ophthalmic slit lamp assembly;

wherein the laser optic axis and a binocular optic axis of said binocular microscope head aligned; and wherein the adaptor includes adjustment means permitting adjustment of the optical head relative to the ophthalmic slit lamp assembly to align the laser optic axis and the binocular optic axis to an optic axis of a slit lamp of the slit lamp assembly.

2. The optical head of claim 1 further comprising a power supply providing power to the laser head.

3. The optical head of claim 1 further comprising control means for controlling operation of the laser head including power, exposure time and pulse duration.

4. The optical head of claim 1 wherein the adaptor is formed from a base member and a frame member, said frame member being movable relative to said base member.

5. The optical head of claim 4 further comprising a locking screw for locking the frame member and base member against relative movement.

6. The optical head of claim 1 wherein the adaptor is formed from a base member and a frame member, said frame member being rotatable and translatable relative to said base member.

7. The optical head of claim 1 wherein said optical head is rotatable relative to said ophthalmic slit lamp assembly.

8. The optical head of claim 1 wherein said optical head is rotatable and translatable relative to said ophthalmic slit lamp assembly.

9. The optical head of claim 1 wherein an underside of the base member is shaped to match a shape of a top portion of microscope support arm of the ophthalmic slit lamp assembly.

10. The optical head of claim 1 wherein the optical head is translatable relative to said ophthalmic slit lamp assembly.

11. In combination, a removable optical head, an ophthalmic slit lamp assembly, and an adaptor removably coupling the optical head to the opthalmic slit lamp assembly, said optical head comprising a laser head emitting laser radiation along a laser optic axis, a binocular microscope head coupled to the laser head, and a power supply providing power to the laser head, wherein the laser optic axis and a binocular optic axis of the binocular microscope head are aligned, and wherein the adaptor includes adjustment means permitting adjustment of the optical head relative to the ophthalmic slit lamp assembly to align the laser optic axis and the binocular optic axis to an optic axis of a slit lamp of the slit lamp assembly.

* * * * *